United States Patent [19]

Silver et al.

[11] Patent Number: 5,777,336

[45] Date of Patent: Jul. 7, 1998

[54] BROADBAND HIGH RESOLUTION X-RAY SPECTRAL ANALYZER

[75] Inventors: Eric H. Silver; Mark Legros, both of Berkeley; Norm W. Madden, Livermore; Fred Goulding, Lafayette; Don Landis, Pinole, all of Calif.

[73] Assignee: The Regents of the University of California, Oakland, Calif.

[21] Appl. No.: 538,323

[22] Filed: Oct. 3, 1995

[51] Int. Cl.[6] .................... G01T 1/36; G01T 1/24
[52] U.S. Cl. .................. 250/370.15; 250/336.2; 250/370.01; 250/370.06
[58] Field of Search .................. 250/336.2, 370.15, 250/370.01, 370.06

[56] References Cited

U.S. PATENT DOCUMENTS 4,904,869  2/1990  Schneider .................. 250/336.2
5,389,792  2/1995  DiMarzio et al. .......... 250/370.15 X

*Primary Examiner*—Edward J. Glick
*Attorney, Agent, or Firm*—Henry P. Sartorio; John P. Wooldridge

[57] ABSTRACT

A broad bandwidth high resolution x-ray fluorescence spectrometer has a performance that is superior in many ways to those currently available. It consists of an array of 4 large area microcalorimeters with 95% quantum efficiency at 6 keV and it produces x-ray spectra between 0.2 keV and 7 keV with an energy resolution of 7 to 10 eV. The resolution is obtained at input count rates per array element of 10 to 50 Hz in real-time, with analog pulse processing and thermal pile-up rejection. This performance cannot be matched by currently available x-ray spectrometers. The detectors are incorporated into a compact and portable cryogenic refrigerator system that is ready for use in many analytical spectroscopy applications as a tool for x-ray microanalysis or in research applications such as laboratory and astrophysical x-ray and particle spectroscopy.

18 Claims, 3 Drawing Sheets

BROADBAND HIGH RESOLUTION X-RAY SPECTRAL ANALYZER

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to x-ray spectroscopy, and more specifically, it relates to an x-ray spectral analyzer having high resolution over a broad band of frequencies.

2. Description of Related Art

X-ray spectrometers are powerful tools in many analytical applications. Such analyzers have commonly incorporated diffractometers or ionization detectors as the spectrally resolving elements. Although wavelength dispersive diffractometers provide high resolving power, they are only sensitive in a narrow wavelength range at any one time. A serial scan is necessary to measure a spectrum, thereby making these instruments very inefficient Energy dispersive spectrometers based on semiconductor ionization detectors, on the other hand, can measure a broad spectral band simultaneously. Energy dispersive spectrometers are more efficient than wavelength dispersive diffractometers; however, their resolving power is one or two orders of magnitude less. A detector that combines the best features of these two techniques simultaneously would extend the value of x-ray spectroscopy by significantly improving the efficiency and sensitivity of today's analytical tools.

SUMMARY OF THE INVENTION

It is an object of the present invention to provide a broadband high resolution x-ray spectral analyzer.

The invention is a broad bandwidth high resolution x-ray fluorescence spectrometer with a performance that is superior in many ways to those currently available. One embodiment consists of an array of 4 large area microcalorimeters with 95% quantum efficiency at 6 keV, and it produces x-ray spectra between 0.2 keV and 7 keV with an energy resolution of 7 eV. The resolution is obtained at input count rates per array element of 10 to 50 Hz in real-time, with analog pulse processing and thermal pile-up rejection. This performance cannot be matched by currently available x-ray spectrometers. The detectors are incorporated into a compact and portable cryogenic refrigeration system that is ready for use in many analytical spectroscopy applications as a tool for x-ray microanalysis or in research applications such as laboratory and astrophysical x-ray and particle spectroscopy.

DETAILED DESCRIPTION OF THE INVENTION

The present invention is a new tool for analytical spectroscopy and provides high resolution x-ray spectra without the bandwidth and sensitivity limitations of a crystal spectrometer. A microcalorimeter is incorporated in a stand-alone, compact, robust and portable refrigeration system and produces x-ray spectra between 0.2 keV and 7 keV with an energy resolution of 7–10 eV (~3.5 eV rms) and an efficiency of 95–100%.

In a microcalorimeter, x-ray photons are absorbed and thermalized in a detector that is weakly coupled to a cold bath. The resulting rise in the detector's temperature is measured with a thermal sensor, resulting in a signal proportional to the x-ray energy. Unlike semiconductor ionization spectrometers where the energy resolution is limited partly by electronic noise and partly by the statistical fluctuations between ionizing and phonon (thermal) processes, calorimetric detectors convert all of the absorbed energy to heat. The contribution to the energy resolution from statistical fluctuations is eliminated. Therefore, the energy resolution in a calorimeter is limited by electron noise only, and as a consequence, is independent of energy over the full energy range of the microcalorimeter.

Figure 1:
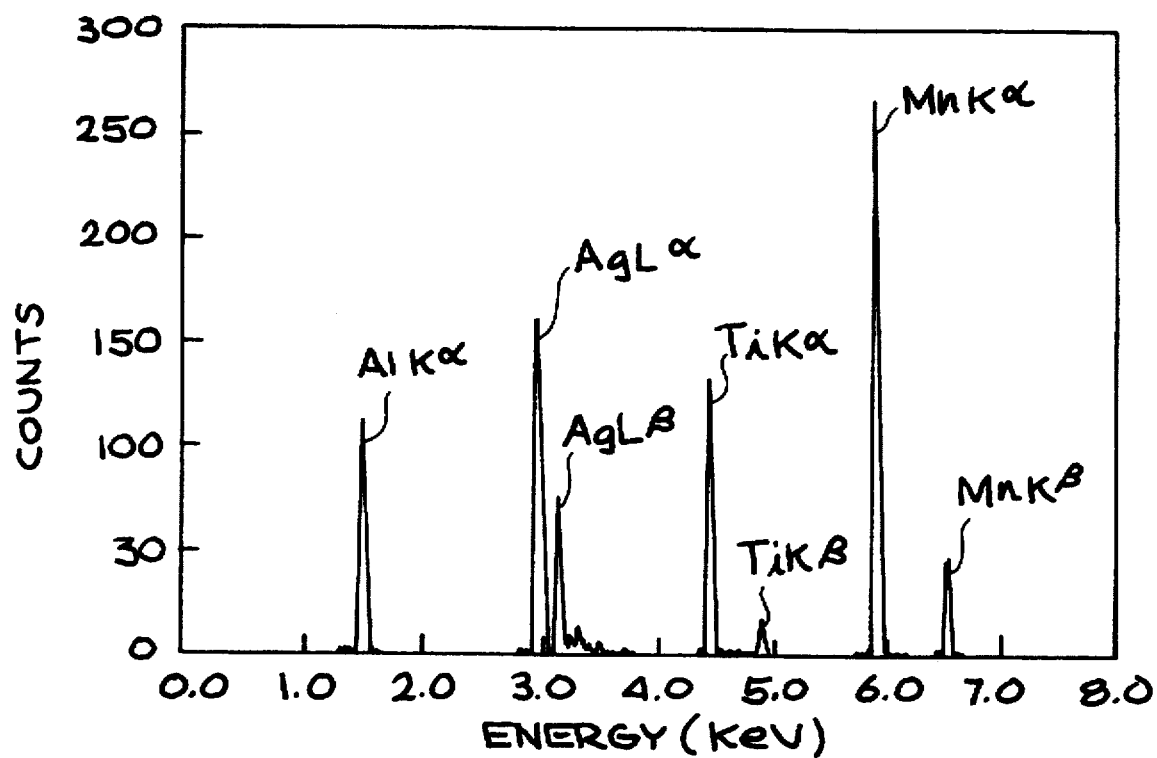
FIG. 1 shows a broad band x-ray fluorescence spectrum made with a single 500 µm×500 µm×7 µm tin (Sn) x-ray absorber attached to an NTD germanium thermistor.
Figure 2:
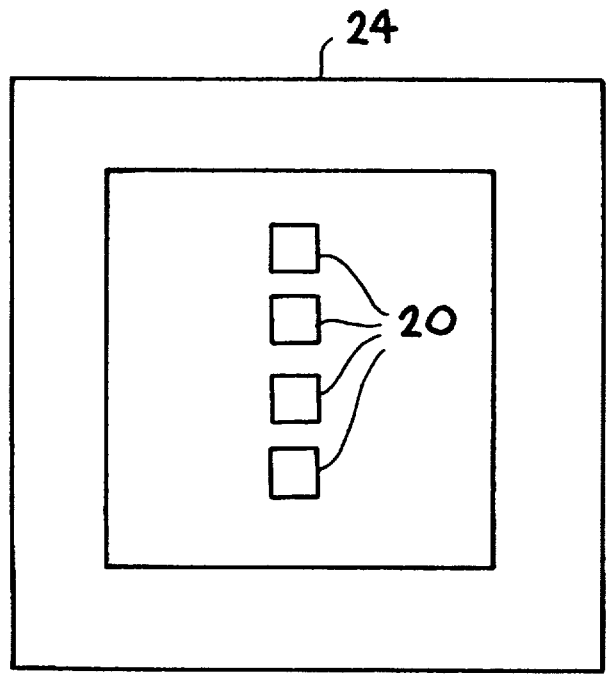
FIG. 2 shows an array of four microcalorimeters.
Figure 4:
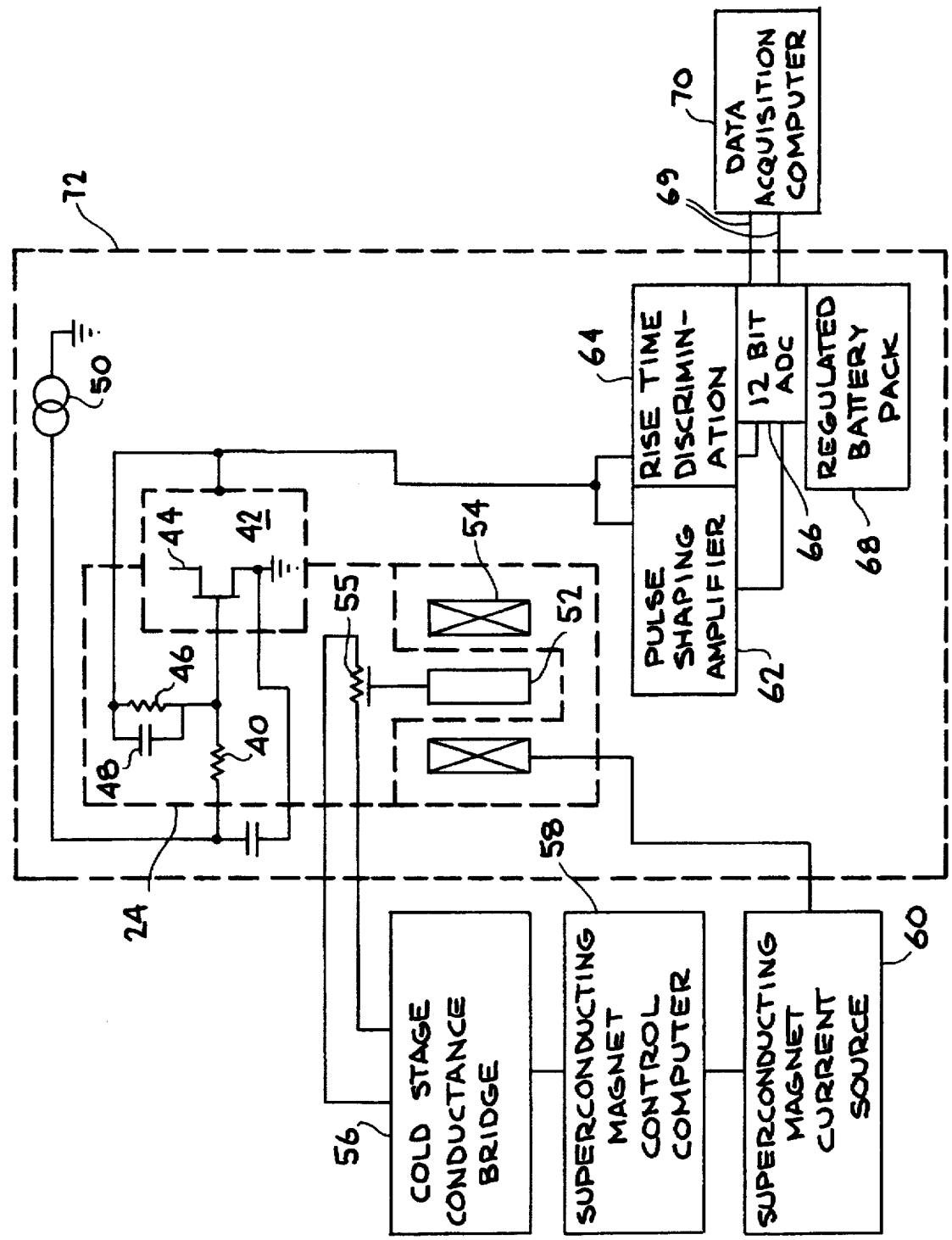
FIG. 4 shows a block diagram of the X-ray spectral analyzer.

FIG. 1 shows a broad band x-ray fluorescence spectrum made with a single 500 µm×500 µm×7 µm tin (Sn) x-ray absorber attached to an NTD germanium thermistor. The x-ray absorber may be a superconducting material and may further comprise a high-Z superconductor (e.g., a Z of 13 or greater). The spectrum was obtained at a count-rate of 10–300 Hz with analog pulse processing that includes thermal pulse pile-up rejection. A portable adiabatic refrigeration system (ARS) accommodates an array of four detectors. FIG. 2 shows an array of four detectors 20, which may be microcalorimeters 20, affixed to a 0.5 mm by 0.5 mm $SiO_2$-coated Sn absorber within refrigeration system 24 (as shown in FIG. 4), which may be a cryogenic cooler for cryogenically cooling the microcalorimeters, where the cryogenic cooler may be a passive cryocooler or a mechanical cryocooler, and where the passive cryocooler uses liquid cryogens. The refrigeration system may be compact, portable and robust, and may consist of an adiabatic refrigerator system or a helium 3 dilution type refrigerator. Detectors 20 may also include a cryogenic detector such as a transition edge sensor, a hot electron microcalorimeter or a superconducting tunnel junction, where the detector is thermally and fixedly attached within and to the refrigeration system.

The cryogenically-cooled microcalorimeters of the present invention satisfy broad bandwidth and high resolution spectroscopy demands. Each microcalorimeter may be operated within the range of 5 mK to 1 K. When operated between these temperatures, these energy dispersive detectors can offer nearly 100% efficiency between 100 eV and 10 keV and an energy resolution approaching several electron volts. Currently available x-ray detectors cannot match such capabilities simultaneously. As a consequence, the performance of this instrument will improve the sensitivity for trace element determination in biological specimens, structural and geological materials as well as strongly contributing to the site remediation of environmental waste. This instrument will set the limits of elemental determination 10 to 100 times below the few parts per million currently achievable in femtogram quantities of various materials.

This can be achieved in conjunction with well-known techniques of x-ray fluorescence, proton-induced x-ray emission (PIXE), or with electron microprobes associated with scanning electron microscopes. The latter application is extremely timely for the semiconductor industry where there is a need for on-line defect review tools of millions of both processed and unprocessed silicon wafers. The improved energy resolution, especially at low electron beam excitation energies, will make it possible to unambiguously assess the level of contamination by extremely small particles (~0.03–0.5 µm). This is extremely important and timely for the national semiconductor industry.

Figure 3:
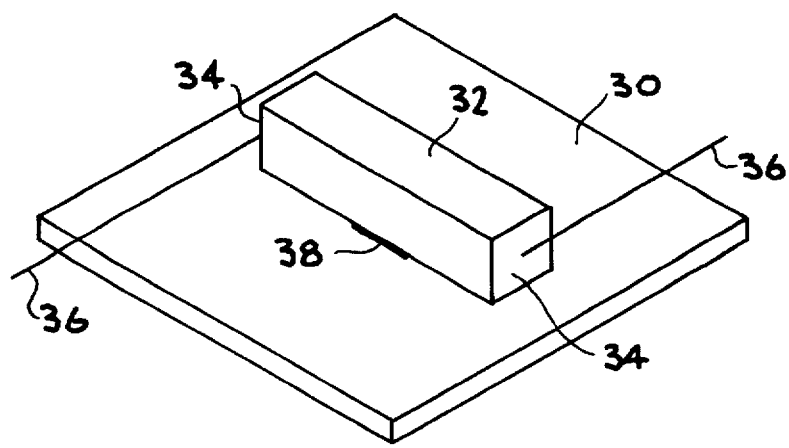
FIG. 3 shows the construction of a single microcalorimeter of the present invention.

FIG. 3 shows the detailed construction of a single microcalorimeter of the present invention. A single 500×500×7 µm$^3$ tin (Sn) x-ray absorber 30 is attached to a neutron transmutation-doped (NTD) germanium thermistor 32 which has two electrical circuit nodes. X-ray absorber 30 may comprise a superconducting material which may have a high Z. The thermistor 32 has dimensions of 100×100×250 µm$^3$, and is implanted at the two ends 34 with boron ions. 3000 angstroms of aluminum are electron beam evaporated onto each end 34 of the thermistor 32. Thermistor 32 may comprise doped epitaxial silicon. The temperature of the NTD germanium is then raised to 300 degrees C. for one hour. This process ensures that the remaining germanium oxide is removed by the electronegative aluminum film. Aluminum wires 17.5 µm in diameter are wedge bonded to the aluminum. The superconducting aluminum wires 36 contain 1% silicon by weight. These aluminum wires 36 serve as the electrical leads, the thermal link to the cold bath and also the mechanical support for the device. The length of each wire is typically ~250 µm. The tin absorber 30 is attached at a single location midway along the NTD thermistor with a spot of glue 38 having a high thermal conductivity (e.g., Epo-Tech 301-2). It may be desirable to attach the thermistor to the x-ray absorber by electroplating. To prevent the possibility that the tin could short-circuit the NTD thermistor, a 1000 Å A layer of silicon dioxide may be sputtered on the tin as an insulating interface. The tin was rolled to the desired thickness and has a quantum efficiency of 95% at 6 keV. In one embodiment, the microcalorimeter may comprise neutron transmutation-doped chips metallurgically bonded to a low thermal conductivity support membrane.

FIG. 4 shows a combined schematic and block diagram of the X-ray spectral analyzer of the present invention. It comprises a microcalorimeter thermistor 40 electrically connected to preamp 42 which has a junction field-effect transistor (JFET) 44, used in a negative voltage feedback circuit with a resistor 46 and a capacitor 48 as the feedback network. A nanoamp current source 50 is electrically connected to the microcalorimeter thermistor 40. Preamp 42 is battery driven by preamp batteries. The spectral analyzer includes an adiabatic demagnetization refrigerator that uses a paramagnetic salt pill 52 such as ferric ammonium alum as the final cold stage. The salt pill 52 sits in the bore of a superconducting magnet 54. Cold stage conductance bridge 56, superconducting magnet control computer 58 and superconducting magnet current source 60 are used to control the temperature and are connected between cold stage thermistor 55 and superconducting magnet 54. The output from preamp 42 is electrically connected to both a pulse shaping amplifier 62 and a rise time discrimination module 64, the outputs from which are electrically connected to a 12 bit analog to digital converter 66 that is electrically powered by a regulated battery pack 68. The outputs from the 12 bit A-D converter 66 are optically coupled by optical coupler 69 to a data acquisition computer 70. An electrostatic shield 72 surrounds components of the X-ray analyzer.

Figure 5:
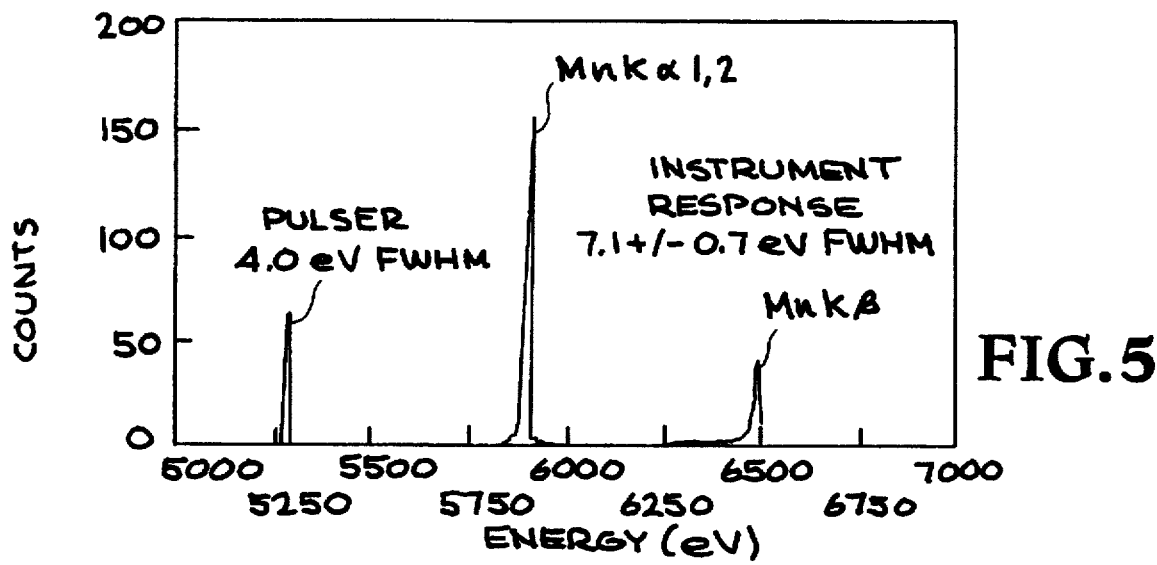
FIG. 5 shows the MnKα and Kβ lines from an $Fe^{55}$ source.
Figure 6:
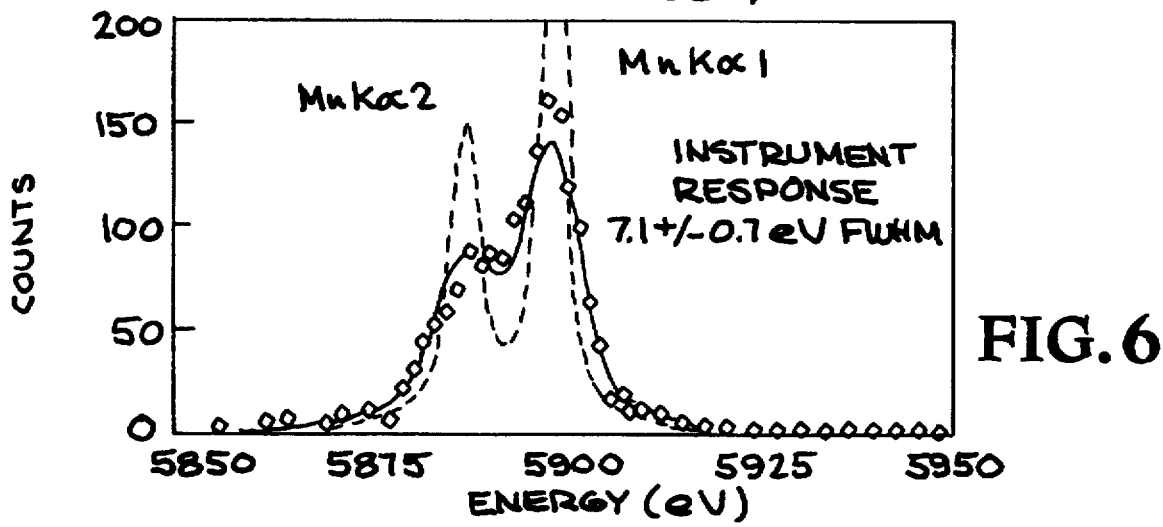
FIG. 6 shows an expanded view of the Kα lines of FIG. 5.

FIGS. 5 and 6 show the 7.1 eV performance of a microcalorimeter of the present invention operating at 80 mK FIG. 5 shows the MnKα and Kβ lines from an Fe$^{55}$ source. The FWHM of the peak labeled "Pulser" is a measurement of the limiting noise of the detector. It corresponds to 4 eV. FIG. 6 shows an expanded view of the K lines, α1 and α2 of FIG. 5. The dotted lines represent the intrinsic line shapes of the two lines which are separated by 11 eV. The diamonds are the data and the solid line is the best fit to the data of an instrument response function with a FWHM of 7.1 eV.

The invention has application in x-ray microanalysis with a scanning electron microscope for the determination of trace element analysis and chemical composition of structural, biological, and geological materials, as a defect review tool in the semiconductor industry in on-line materials processing analysis, and in environmental site remediation. Other uses include x-ray fluorescence spectroscopy and x-ray, gamma-ray, particle, atomic and plasma physics spectroscopy and imaging.

Changes and modifications in the specifically described embodiments can be carried out without departing from the scope of the invention, which is intended to be limited by the scope of the appended claims.

We claim:

1. A broadband, high resolution, X-ray spectral analyzer, comprising a refrigeration system; and
   at least one microcalorimeter comprising:

an x-ray absorber;
   a neutron transmutation-doped (NTD) germanium thermistor with two electrical circuit nodes, wherein said thermistor is fixedly and thermally connected to said x-ray absorber;
   an electrical contact fixedly and electrically connected to each electrical circuit node of said two electrical circuit nodes of said thermistor, wherein said electrical contact comprises boron ion implants and further comprises a layer of aluminum; and
   a superconducting wire bonded to each said electrical contact, wherein said microcalorimeter is located within said refrigeration system, wherein said two electrical circuit nodes, said aluminum layer and said superconducting wire are fixedly and thermally connected to said thermistor and said refrigeration system.

2. The broadband, high resolution, X-ray spectral analyzer of claim 1, wherein said x-ray absorber comprises superconductor material.

3. The broadband, high resolution, X-ray spectral analyzer of claim 2, wherein said superconductor material comprises a high-Z superconductor.

4. The broadband, high resolution, X-ray spectral analyzer of claim 1, wherein said x-ray absorber comprises a metal.

5. The broadband, high resolution, X-ray spectral analyzer of claim 1, wherein said nodes of said NTD germanium thermistor have been processed by raising their temperature to 300 degrees C. for about one hour.

6. The broadband, high resolution, X-ray spectral analyzer of claim 1, wherein said thermistor is attached to said x-ray absorber by electroplating.

7. The broadband, high resolution, X-ray spectral analyzer of claim 1, wherein said thermistor is attached to said x-ray absorber at a single point midway along the length of said thermistor.

8. The broadband, high resolution, X-ray spectral analyzer of claim 1, wherein said superconducting wire contains silicon.

9. The broadband, high resolution, X-ray spectral analyzer of claim 8, wherein said superconducting wire is up to about 250 micrometers in length.

10. The broadband, high resolution, X-ray spectral analyzer of claim 1, wherein said x-ray absorber comprises a layer of about 1000 angstroms of silicon dioxide.

11. The broadband, high resolution, X-ray spectral analyzer of claim 1, wherein said layer of aluminum comprises about 3000 Å of aluminum deposited by electron-beam evaporation, wherein said superconducting wire is wedge-bonded to each said electrical contact.

12. The broadband, high resolution, X-ray spectral analyzer of claim 1, wherein said refrigeration system includes a cryocooler for cooling said at least one microcalorimeter, wherein said cryocooler is selected from a group consisting of a passive cryocooler and a mechanical cryocooler, wherein said passive cryocooler comprises liquid cryogens.

13. The broadband, high resolution, X-ray spectral analyzer of claim 1, wherein said refrigeration system comprises an adiabatic refrigerator system.

14. The broadband, high resolution, X-ray spectral analyzer of claim 1, wherein said at least one microcalorimeter is electrically connected to a pulse processing system.

15. The broadband, high resolution, X-ray spectral analyzer of claim 1, wherein said refrigerator system comprises a helium 3 dilution type refrigerator for operating said at least one microcalorimeter at cryogenic temperatures.

16. The broadband, high resolution, X-ray spectral analyzer of claim 1, wherein said thermistor comprises neutron transmutation-doped chips metallurgically bonded to a low thermal conductivity support membrane.

17. The broadband, high resolution, X-ray spectral analyzer of claim 1, wherein said at least one microcalorimeter comprises an array of four microcalorimeters, and wherein each microcalorimeter of said at least one microcalorimeter has 95% quantum efficiency at 6 keV for production of x-ray spectra between 0.2 keV and 7 keV with an energy resolution of between 7 eV and 10 eV obtained at input count rates between 10 and 50 Hz in real-time, using analog pulse processing and thermal pile-up rejection.

18. A broadband, high resolution, X-ray spectral analyzer within a refrigerator system, comprising:

an x-ray absorber comprising a high Z superconductor;

at least one cryogenic detector attached to said x-ray absorber, wherein said at least one cryogenic detector is thermally connected to said refrigerator system, wherein said at least one cryogenic detector is selected from a group consisting of a transition edge sensor, a hot electron microcalorimeter and a superconducting tunnel junction;

electrical contacts electrically connected to each end of said at least one cryogenic detector, wherein said electrical contacts comprise boron ion implants and further comprise 3000 Å of aluminum deposited by electron-beam evaporation; and wedge-bonded aluminum wires electrically connected to said electrical contacts.

* * * * *